United States Patent [19]

Palackal et al.

[11] Patent Number: 5,401,817
[45] Date of Patent: Mar. 28, 1995

[54] OLEFIN POLYMERIZATION USING SILYL-BRIDGED METALLOCENES

[75] Inventors: Syriac J. Palackal, Bartlesville, Okla.; Helmut G. Alt, Bayreuth, Germany; Konstantinos Patsidis, Bayreuth, Germany; Tara G. Hill, Fairfield, Ohio; Gil R. Hawley, Dewey; Peter P. Chu, Bartlesville, both of Okla.; M. Bruce Welch; Rolf L. Geerts, both of Bartlesville, Okla.

[73] Assignee: Phillips Petroleum Company, Bartlesville, Okla.

[21] Appl. No.: 64,630

[22] Filed: May 20, 1993

Related U.S. Application Data

[63] Continuation-in-part of Ser. No. 734,853, Jul. 23, 1991, and a continuation-in-part of Ser. No. 984,054, Nov. 30, 1992, which is a continuation-in-part of Ser. No. 697,363, May 9, 1991, Pat. No. 5,191,132.

[51] Int. Cl.⁶ .................. C08F 4/64; C08F 110/06
[52] U.S. Cl. ..................... 526/127; 526/126; 526/160; 526/170; 526/351; 556/111; 556/12
[58] Field of Search ............... 526/126, 127, 160, 170, 526/351

[56] References Cited

U.S. PATENT DOCUMENTS

| | | | |
|---|---|---|---|
| 3,364,190 | 1/1968 | Emrick | 526/139 |
| 3,426,069 | 2/1969 | Fritz et al. | 260/562 |
| 4,794,096 | 12/1988 | Ewen | 502/117 |
| 4,808,561 | 2/1989 | Welborn, Jr. | 502/104 |
| 4,892,851 | 1/1990 | Ewen et al. | 502/104 |
| 4,931,417 | 6/1990 | Miya et al. | 502/117 |
| 5,017,714 | 5/1991 | Welborn, Jr. | 556/12 |
| 5,049,535 | 9/1991 | Resconi et al. | 502/117 |
| 5,071,808 | 12/1991 | Antberg et al. | 502/107 |
| 5,087,677 | 2/1992 | Brekner et al. | 526/160 |
| 5,120,867 | 6/1992 | Welborn, Jr. | 556/12 |
| 5,132,381 | 7/1992 | Winter et al. | 526/160 |
| 5,145,819 | 9/1992 | Winter et al. | 502/117 |
| 5,225,501 | 7/1993 | Fujita et al. | 526/127 |
| 5,252,677 | 10/1993 | Tomita et al. | 526/170 X |
| 5,276,208 | 1/1994 | Winter et al. | 556/53 |

FOREIGN PATENT DOCUMENTS

| | | | |
|---|---|---|---|
| 0387609 | 9/1990 | European Pat. Off. | |
| 459264 | 5/1991 | European Pat. Off. | |
| 498675 | 2/1992 | European Pat. Off. | |
| 0485821A1 | 5/1992 | European Pat. Off. | |
| 0503422 | 9/1992 | European Pat. Off. | 526/160 |
| 0528287 | 2/1993 | European Pat. Off. | 526/160 |
| 577581 | 6/1993 | European Pat. Off. | |

OTHER PUBLICATIONS

Journal of the American Chemical Society, vol. 95, No. 5, Mar. 7, 1973, pp. 1503–1508.
Journal of the American Chemical Society, vol. 78, (1956), pp. 3530–3533 Chemical Abstracts, vol. 119, (1993).
Inorganic Chemistry, vol. 27, No. 18 (1988), pp. 3069–3075.
Organometallics, vol. 119, (1993), p. 921.
Chemical Abstracts, vol. 51.
Chemical Abstracts, vol. 99, (1983).
Chemical Abstracts, vol. 118, 1993.
J. Chem. Soc., 76, (1954), pp. 2027–2030.
Journal of Organometallic Chemistry, 172 (1079) pp. 11–19.

Primary Examiner—Fred Teskin
Attorney, Agent, or Firm—Edward L. Bowman

[57] ABSTRACT

Fluorenyl-containing silyl bridged metallocenes, the process of using such metallocenes to polymerize olefins, and the resulting unusual syndiotactic polypropylene are disclosed.

14 Claims, 6 Drawing Sheets

OLEFIN POLYMERIZATION USING SILYL-BRIDGED METALLOCENES

This application is a continuation-in-part of U.S. application Ser. No. 07/734,853, filed Jul. 23, 1991, and a continuation-in-part of U.S. application Ser. No. 07/984,054, filed Nov. 30, 1992, which is a continuation-in-part of U.S. application Ser. No. 07/697,363, filed May 9, 1991, now U.S. Pat. No. 5,191,132. The disclosures of all three of the aforementioned applications are incorporated herein by reference.

FIELD OF THE INVENTION

The present invention relates to metallocenes. In another aspect, the present invention relates to the polymerization of olefins using metallocenes. In still another aspect, the present invention relates to novel olefin polymers prepared by polymerization using the metallocene. More particularly, the present invention relates to bridged sandwich-bonded metallocenes in which the bridge is a diorgano silyl bridge.

BACKGROUND OF THE INVENTION

It is well known that many metallocenes can be useful for the polymerization of olefins. Particularly it has been noted that metallocenes can be combined with aluminoxanes to produce catalyst systems of high activity for the production of polyolefins. A particularly interesting type of metallocene for olefin polymerization is the so-called bridged sandwich-bonded metallocene in which the ligand of the metallocene comprises two cyclopentadienyl-type groups connected through a bridging group. Some of the bridged sandwich-bonded metallocenes when used in the polymerization of olefins having three or more carbon atoms have been found to be useful for producing polymers having different types of microstructure as reflected by tacticity as determined by infrared (IR) and nuclear magnetic resonance (NMR) spectroscopic techniques. A discussion of such techniques is disclosed in Zambelli et al, *J. Polym. Sci. Part C,* 84, 1488, (1962); Lotz et al, *Macro Molecules,* 21, 2375, (1988); Haftka et al, *J. Macromol. Sci. Phys.,* 830, 319, (1991); and Youngman et al, *Macromol. Res.,* 2, 33 (1967). A particularly good description of the NMR technique is contained in Chapter 3 of the book "Chain Structure and Conformation of Macromolecules" by Frank A. Bovey (Academic Press, 1982).

It is well known in the art that the microstructure tacticity of a polyolefin molecule can have a significant effect upon the physical properties of the polymer. Other things which affect the polymer properties include the type of monomer, and comonomer if employed, the weight average molecular weight ($M_w$) of the polymer, the molecular weight distribution, and the composition distribution of the resin. Accordingly, for producing commercially desirable polymers, it is important to find metallocene catalysts which give the desired combination of polymer properties plus commercially practical polymerization activities.

A wide range of sandwich-bonded bridged metallocenes have been at least proposed in the open literature and the patent literature and there have been some studies of the effects of varying the structure of the ligand used in the metallocene. One example of such a study is disclosed in the *New Journal of Chemistry*, Vol. 14, No. 6–7, pages 499–503 (1990). While the patent literature contains broad assertions regarding the particular types of polymers that will be produced with specific types of metallocenes, subsequent work has revealed that those generalizations are too broad.

For example, while U.S. Pat. Nos. 4,794,096 and 4,769,510 teach that bridged chiral, stereorigid metallocene catalysts are capable of producing polymers having high levels of isotactic microstructure, the only actual examples are ethylene bridged bisindenyl or bis tetrahydroindenyl metallocenes. Further U.S. Pat. No. 4,892,851 shows that that the bridged, chiral, sterorigid metallocene cyclopentadienyl isopropylidene fluorenyl zirconium dichloride produces highly syndiotatic polypropylene rather than isotactic polyproplyene. Also, Dr. Abbas Razavi in an SPO 92 paper of September 1992 reported that the bridged, chiral, stereorigid metallocene rac[bis(3-methyl indenyl)ethylene]zirconium dichloride yields a highly amorphous polyproylene rather than an isotactic polypropylene. Further, while U.S. Pat. No. 4,892,551 contains the broad assertion that bridged metallocenes having two sterically different cyclopentadienyl type groups will produce highly syndiotatic polypropylene, the published EPC Application 423,101 demonstrates that the metallocene 3-methylcyclopentadienyl isopropylidene fluorenyl zirconium dichloride does not produce a syndiotactic polypropylene but rather an amorphous polypropylene referred to as hemiisotactic.

Although the above-mentioned *New Journal of Chemistry* article discloses two metallocenes having a silyl bridge, it does not contain any information regarding the effects a silyl bridge would have in a metallocene in which the ligand also has a fluorenyl radical. In addition, there are a number of patents which at least envision the possibility of various silyl bridged metallocenes including metallocenes having fluorenyl in the ligand; however, so far as the applicants are aware, there are no publications which discuss the results actually obtained with a silyl bridged sandwich-bonded metallocene which includes fluorenyl in the ligand. Accordingly, there is no actual evidence as to actually what kind of polymer would be produced with the wide range of silyl bridged fluorenyl-containing metallocenes that have been postulated as possible metallocene catalysts.

An object of the present invention is to provide new types of silyl bridged sandwich-bonded metallocene catalysts.

Another object of the present invention is to provide a process for polymerizing olefins using the special silyl bridged metallocenes.

In accordance with yet another aspect of the present invention, there is provided a process for producing novel syndiotactic polymers, particularly syndiotactic polypropylene polymers having unexpectedly low density and low stiffness and tensile properties for their observed degree of syndiotacticity.

SUMMARY OF THE INVENTION

Figure 1:
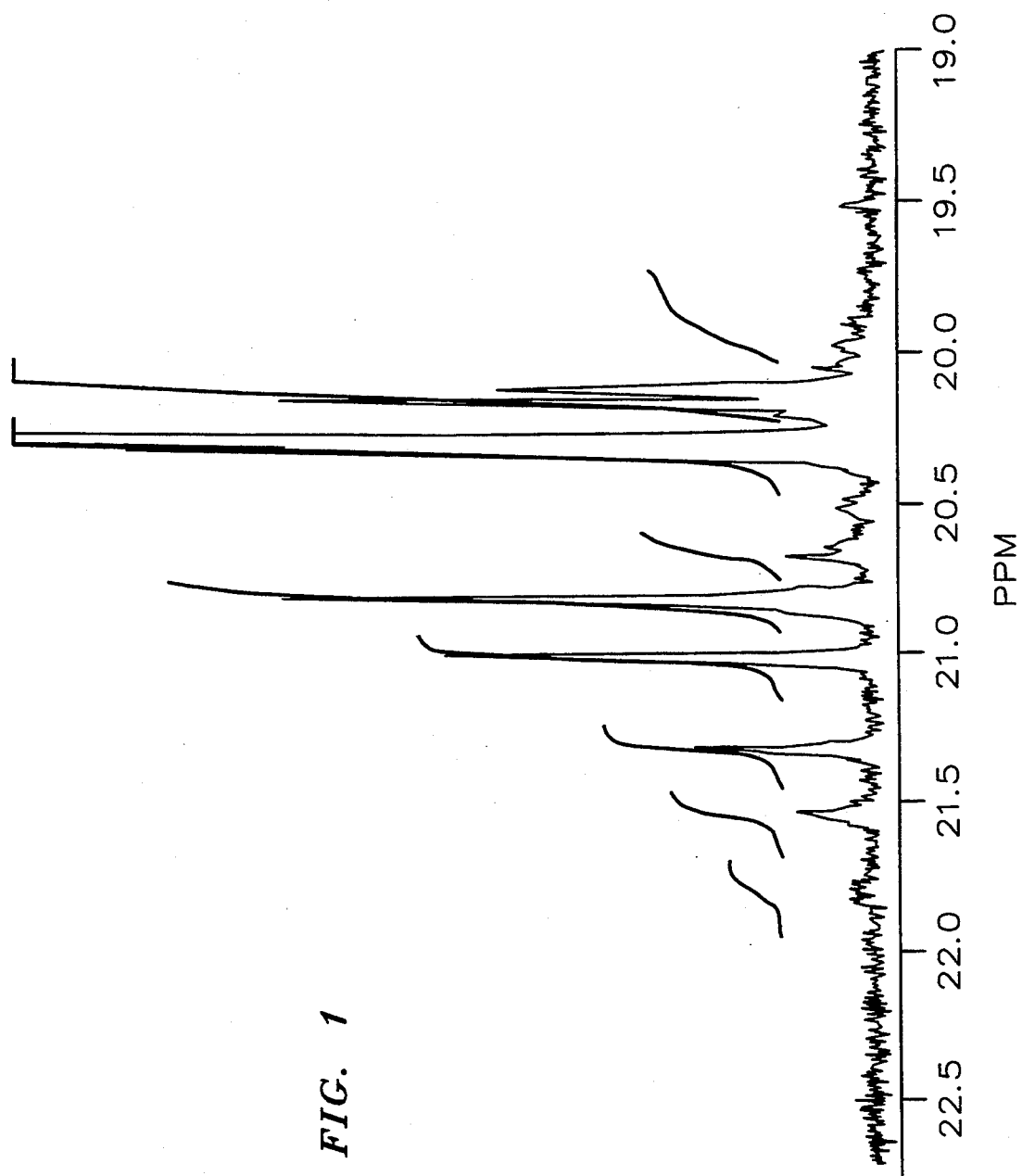
FIG. 1 is a $C_{13}$NMR spectra of a syndiotactic polypropylene produced using (fluorenyl)dimethylsilyl(cyclopentadienyl)zirconium dichloride.

In accordance with the present invention, there is provided metallocene olefin polymerization catalysts comprising bridged sandwich-bonded metallocenes of a metal selected from Group IVB of the Periodic Table in which the organic ligand is selected from compounds of the formula

wherein Z and Z' are different, Z is an unsubstituted fluorenyl radical or a symmetrically substituted fluorenyl radical and Z' is an unsubstituted cyclopentadienyl radical, a symmetrically substituted cyclopentadienyl radical, an unsubstituted fluorenyl radical, or a symmetrically substituted fluorenyl radical; each R' is the same or different and is selected from organo radicals having 1 to 20 carbon atoms. In accordance with yet another aspect of the present invention, there is provided a process for polymerizing an olefin comprising contacting the olefin under suitable polymerization conditions with a catalyst system comprising the inventive bridged sandwich-bonded metallocene. Still further in accordance with the present invention, there is provided a novel homopolymer of propylene which is substantially syndiotactic but which has properties that are significantly different than syndiotactic polypropylene produced with prior art metallocenes such as the metallocene of the actual examples of U.S. Pat. No. 4,892,851, namely, isopropyl(cyclopentadienyl-1-fluorenyl)zirconium dichloride which can also be called 1-cyclopentadienyl-1-fluorenyl-1,1-dimethyl methane zirconium dichloride.

DETAILED DESCRIPTION OF THE INVENTION

As noted above, the organic ligand used in making the metallocenes of this invention is one in which Z and Z' are different. Z is selected from an unsubstituted fluorenyl radical or a symmetrically-substituted fluorenyl radical. Unless otherwise indicated, the term "fluorenyl" as used herein refers to the 9-fluorenyl radical as described in commonly owned U.S. Pat. No. 5,191,132. The Z' of the organic ligand is selected from unsubstituted cyclopentadienyl or fluorenyl radicals or symmetrically substituted cyclopentadienyl or fluorenyl radicals.

The term "symmetrically substituted" as used herein refers to those radicals which have substituents on opposite positions of the cyclopentadienyl-type radical, such as 2,7-dialkylfluorenyl; 3,6-dialkylfluorenyl; 2,5-dialkylcyclopentadienyl; 3,4-dialkylcyclopentadienyl; and the like. The substituents on the organic radicals Z or Z' can vary over a wide range and can be basically any substituent which does not interfere with the results desired. The currently preferred alkyl substituents are radicals having 1 to 20 carbon atoms, more preferably, 1 to 6 carbon atoms, and most preferably 1 to 4 carbon atoms. Most preferably, all the substituents on a given substituted Z or substituted Z' are the same. For example, 2,7-dimethylfluorenyl; 2,7-di-t-butylfluorenyl; 2,7-diphenylfluorenyl; and the like.

The R' radicals of the silyl bridge can each be the same or different. They are preferably selected from organo radicals having 1 to 20 carbon atoms, more typically alkyl radicals having 1 to 6 atoms and aryl radicals having 6 to 10 atoms. The method for preparing such silyl-bridged ligands is disclosed in the commonly owned U.S. patent application Ser. No. 07/984,054 and U.S. Pat. No. 5,191,132. One technique involves reacting a substituted or unsubstituted fluorenyl compound with an alkali metal alkyl to produce the corresponding fluorenyl anion. The resulting fluorenyl anion is then contacted under suitable reaction conditions with a silyl compound having at least two halogens. An example would be the dihalosilyl compounds of the formula

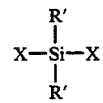

wherein each R' is individually selected from an organo radical containing 1 to 20 carbon atoms, and each X is individually selected from Cl, Br, or I. In such compounds, preferably at least one of the R' groups is a $C_1$-$C_{10}$ group, a $C_1$-$C_{10}$ fluoro alkyl group, a $C_6$-$C_{10}$ aryl group, a $C_6$-$C_{10}$ fluoro aryl group, a $C_1$-$C_{10}$ alkoxy group, a $C_2$-$C_{10}$ alkenyl group, a $C_7$-$C_4$ aryl alkyl group, a $C_8$-$C_{20}$ aryl alkenyl group, or a $C_7$-$C_{20}$ alkyl aryl group. It is also within the scope of the invention for the two R' groups to be joined to form a heterocyclic ring containing Si.

The fluorenyl anion is reacted with the halosilyl compound in the presence of a suitable liquid diluent to produce a fluorenyl silyl halide. This product can then be reacted with an anion of Z' to produce the desired end product.

The alkali metal alkyls employed for producing the anions of Z and Z' would typically be selected from sodium, potassium, and lithium alkyls having 1 to 8, more preferably 1 to 4 carbon atoms. Typically, the anion would be formed by dissolving or dispersing the Z or Z' compound in a suitable liquid diluent and then adding the alkali metal alkyl. Typically, in the past such techniques have used as the liquid diluent a polar solvent, for example, tetrahydrofuran. The present applicants have found that non-polar solvents, such as alkanes, cycloalkanes, aromatic hydrocarbons, and non-cyclic ethers can also be employed. Some specific examples include toluene, hexane, and diethyl ether. The reaction between the fluorenyl-containing Z anion and the silyl halide compound can also be in any suitable liquid. Examples include diethylether, hydrocarbons such as pentene, hexene, and toluene, and mixtures thereof. It has been found desirable to employ a relatively non-polar liquid solvent. Preferably the Z anion is gradually added to a stirred solution of the silyl halide compound. If Z is 2,7-di-tert-butyl fluorenyl, it is preferred to use diethyl ether rather than pentane. The product can be recovered and purified by washing with aqueous saturated ammonium chloride solution, washing with water and then separating the organic phase. The product can be purified by washing with a suitable liquid, dissolving the product and re-crystallizing the product.

The reaction pressure and temperature for the ligand and metallocene preparations disclosed herein are not particularly critical and can vary over a wide range depending upon the results desired. Atmospheric pressures are currently preferred although higher and lower pressures could be employed. Typically, the reaction temperatures will be in the range of from about −100° C. to about 100° C. Generally, it is convenient to carry out the reactions at ambient temperatures in the range of about 15° C. to about 30° C. In preparing the compound of the formula

it is generally preferred that the molar ratio of the organic Z anion to the silyl halide compound be no greater than about 1:1. Preferably an excess of silane is used at high dilution in the liquid.

The Z silyl halide compound can then be reacted with an alkali metal salt of the selected Z' compound in a suitable liquid diluent. The liquid diluent used can be any suitable liquid, examples include those liquids named above as suitable for forming the fluorenyl silyl halide compound, with or without polar additives such as propylene carbonate, hexamethylphosphoric triamide (HMPT), etc. Such polar additives have been noted to increase the reaction rate. The resulting product can be recovered and purified using techniques of the type mentioned above for the fluorenyl silyl halide compound.

The inventive metallocenes can be prepared by reacting a di-alkali metal salt of the silyl bridged fluorenyl-containing ligands with a suitable transition metal compound in a suitable liquid under suitable reaction conditions.

The term "transition metal compound" as used herein includes compounds of the formula $MeQ_k$ wherein Me is a metal selected from Group IVB metals of the Periodic Table. The currently preferred metals include titanium, zirconium, and hafnium. Each Q is individually selected from a hydrocarbyl radical, such as, for example aryl, alkyl, alkenyl, alkaryl, or arylalkyl radical having from 1 to 20 carbon atoms, a hydrocarbyloxy radicals having 1 to 20 carbons, or a halogen. Some non-limiting examples of such transition metal compounds include zirconium tetrachloride, hafnium tetrachloride, cyclopentadienyl zirconium trichloride, fluorenyl zirconium trichloride, 3-methylcyclopentadienyl zirconium trichloride, 4-methylfluorenyl zirconium trichloride, and the like. It is currently preferred to use inorganic transition metal halides.

Metallocenes of the formula $ZSi(R')_2Z'MeQ_k$ in which one or more of the Q's is other than a halogen can be readily prepared by reacting a halide form of the metallocene with an alkali metal salt of the hydrocarbyl or hydrocarbyloxy radical under conditions as have been used in the past for forming such ligands and prior art metallocenes. See for example, the *Journal of Organometallic Chemistry*, 113, 331–339 (1976). Another approach involves reacting a compound of the formula $MQ_k$ wherein at least one Q is a hydrocarbyl or hydrocarbyloxy radical with the alkali metal salt of the bridged fluorenyl compound.

One embodiment of the present invention involves carrying out the reaction of the fluorenyl-containing ligand salt and the transition metal compound in the presence of a liquid diluent which is non-halogenated and non-coordinating toward the transition metal compound. Examples of such liquids include hydrocarbons such as toluene, pentane, or hexane as well as non-cyclic ether compounds such as diethylether. It has been found that the use of such non-halogenated, non-coordinating liquids generally allows one to obtain larger amounts of substantially pure metallocenes and in a more stable form; and also allows the reaction to be conducted under higher temperature conditions, than when THF is used as the liquid diluent. In an especially preferred embodiment, the fluorenyl-containing ligand salt that is used at the ligand is also prepared in a liquid diluent that is non-halogenated and non-coordinating toward the transition metal.

The method of reacting the alkali metal salt of the bridged fluorenyl ligand with the transition metal compound is disclosed in commonly owned copending application Ser. No. 07/734,853. The molar ratio of the alkali metal alkyl to the cyclopentadienyl-type radicals present in the ligand can vary, generally however, the ratio will be in the range of about 0.5/1 to about 1.5/1, still more preferably about 1:1. Typically, the alkali metal of the alkali metal alkyl would be selected from sodium, potassium, and lithium and the alkyl group would have from 1 to 8 carbon atoms, more preferably 1 to 4 carbon atoms. The molar ratio of the bridged fluorenyl ligand salt to the transition metal compound can also vary over a wide range depending upon the results desired. Typically, however, the molar ratio of the bridged fluorenyl compound to the transition metal compound is about 1:1.

The resulting metallocene can be recovered and purified using conventional techniques known in the art such as filtration, extraction, crystallization, and re-crystallization. It is generally desirable to recover the metallocene in a form that is free from any substantial amount of by-product impurities. Accordingly, re-crystallization and fractional crystallization to obtain relatively pure metallocenes is desirable. Dichloromethane has been found to be particularly useful for such re-crystallizations. Since the stability of the various metallocenes varies, it is generally desirable to use the metallocenes soon after their preparation or at least to store the metallocenes under conditions favoring their stability. For example, the metallocenes can generally be stored at low temperature, i.e., below 0° C. in the absence of oxygen or water.

The fluorenyl silyl metallocenes of the present invention can be activated to produce a catalyst system suitable for the polymerization of olefin monomers. It is contemplated that the inventive fluorenyl silyl metallocenes can be activated using generally any of the techniques that in the past have been suitable for other similar metallocenes, including using cocatalyst or even activation using a stable non-coordinating counter anion technique such as disclosed in U.S. Pat. No. 5,155,080, e.g. using triphenyl carbenium tetrakis(pentafluorophenyl)boronate. Another example would be the use of a mixture of trimethylaluminum and dimethylfluoroaluminum such as disclosed by Zambelli et al, *Macromolecules*, 22, 2186 (1989). In such processes, the metallocene or the co-catalyst can be employed on a solid insoluble particulate support.

Examples of typical co-catalysts include generally any of those organometallic co-catalysts which have in the past been employed in conjunction with transition metal containing olefin polymerization catalysts. Some typical examples include organometallic compounds of metals of Group IA, IIA, and IIIB of the Periodic Table. Examples of such compounds have included organometallic halide compounds, organometallic hydrides, and even metal hydrides. Some specific examples include triethylaluminum, triisobutylaluminum, diethylaluminium chloride, diethylaluminum hydride, and the like.

The currently most preferred co-catalyst is an aluminoxane. Such compounds include those compounds having repeating units of the formula

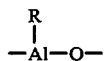

where R is an alkyl group generally having 1 to 5 carbon atoms. Aluminoxanes, also sometimes referred to as poly(hydrocarbyl aluminum oxides) are well known in the art and are generally prepared by reacting an organo hydrocarbylaluminum compound with a water source. Such preparation techniques are disclosed in U.S. Pat. Nos. 3,242,099 and 4,808,561, the disclosures of which are incorporated herein by reference. The currently preferred co-catalysts are prepared either from trimethylaluminum or triethylaluminum, sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

The fluorenyl-containing metallocenes in combination with an aluminoxane co-catalyst can be used to polymerize olefins. Such polymerizations can be carried out in a homogeneous system in which the catalyst and co-catalyst are soluble; however, it is within the scope of the present invention to carry out the polymerizations in the presence of supported forms of the catalyst and/or co-catalyst in a slurry, solution, or gas phase polymerization. It is within the scope of the invention to use a mixture of two or more fluorenyl-containing metallocenes or a mixture of an inventive fluorenyl-containing metallocene with one or more other cyclopentadienyl-type metollocenes.

The fluorenyl-containing metallocenes when used with aluminoxane are particularly useful for the polymerization of mono-unsaturated aliphatic alpha-olefins having 2 to 10 carbon atoms. Examples of such olefins include ethylene, propylene, butene-1, pentene-1, 3-methylbutene-1, hexene-1, 4-methylpentene-1, 3-ethylbutene-1, heptene-1, octene-1, decene-1, 4,4-dimethyl-1-pentene, 4,4-diethyl-1-hexene, 3-4-dimethyl-1-hexene, and the like and mixtures thereof. The catalysts are useful for preparing copolymers of ethylene and propylene or of ethylene or propylene and a higher molecular weight olefin. In some preferred embodiments, generally a minor amount, i.e. no more than about 12 mole percent, more typically less than about 10 mole percent, of the higher molecular weight olefin is used. The catalysts are particularly useful for preparing homopolymers of alpha-olefin having 3 or more carbon atoms per molecule.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

When aluminoxane is used as cocatalyst, generally the molar ratio of the aluminum in the aluminoxane to the transition metal in the metallocene would be in the range of about 0.1:1 to about $10^5$:1 and more preferably about 5:1 to about $10^4$:1. As a general rule, the polymerizations would be carried out in the presence of liquid diluents which do not have an adverse affect upon the catalyst system. Examples of such liquid diluents include butane, isobutane, pentane, hexane, heptane, octane, cyclohexane, methylcyclohexane, toluene, xylene, and the like. The polymerization temperature can vary over a wide range, temperatures typically would be in the range of about $-60°$ C. to about $320°$ C., more preferably in the range of about $20°$ C. to about $160°$ C. Typically the pressure would be in the range of from about 1 to about 500 atmospheres or greater. For particular results, it is sometimes useful to conduct the polymerizations in the presence of hydrogen.

The syndiotactic polymers produced according to the invention will have a wide range of applications based upon their physical properties. They can be molded by heat to form shaped objects. They can be used for blending with polymers of different tacticity to vary the properties of such polymers and they can be used to form fibers or filaments.

A further understanding of the present invention and its objects and advantages will be provided by the following examples. In the following examples where information is given about the microstructure of polymers as determined by $C_{13}NMR$, the spectra were taken using standard accepted spectroscopy techniques. The polymer was dissolved in trichlorobenzene and the spectra was taken with respect to an internal standard relative to hexamethylsiloxane which has a known reference point relative to tetramethyl silane. From the observed integrals of the relevant peaks, the details regarding the microstructure are calculated.

Meso Content = $(mm) + \frac{1}{2}(mr)$
Racemic Content = $(rr) + \frac{1}{2}(mr)$
Isotacticity = % $(mm)$
Heterotyacticity = % $(mr)$
Syndiotacticity = % $(rr)$ Randomness Index = $\frac{(mr)100}{2(m)(r)}$ Average Isotactic Block Length = $1 + \frac{2(mm)}{(mr)}$ Average Syndiotactic Block Length = $1 + \frac{2(rr)}{(mr)}$ For more detail regarding the determination of these values, reference can be made to Chapter 3 of the aforementioned book by Frank A. Bovey.

In some of the following examples reference is made to Xylene Solubles and Heptane Solubles.

The Xylene Solubles, i.e. wt % Xylene Solubles, test involves adding 1 gram of the polymer to a centrifuge tube containing 100 ml of xylene. The tube is placed in a heater-evaporator maintained at 140° C. and the liquid is stirred occasionally. After 15 minutes the tube is removed from the heater and allowed to cool at room temperature for 15 minutes and then cooled for 30 minutes in an ice bath. The tube is then centrifuged at 1900 rpm for 15 minutes. Then 25 ml of the supernatant xylene solution is placed in a tared aluminum dish and the xylene evaporated by placing the dish in the evaporator for 30 minutes. The term "wt % xylene solubles" refers to the grams of polymer in the dish times four divided by the grams of original polymer, i.e. 1, times 100.

The Heptane Solubles, i.e. wt % Heptane Solubles, test involves extraction of the polymer with heptane in a Soxhlet extractor apparatus. About 0.4 grams of polymer is placed in a sample tube with glass wool plugs at each end. The tube and the plugs have been previously weighed. The actual weight of the polymer in the tube is then determined. The tube is placed in the Soxhlet extractor. The boiling flask is filled about half full of heptane. Boiling chips are present in the flasks. The extractor is assembled on top of the boiling flask and the condensor is assembled on top of the extractor. Cooling water is circulated through the condensor. The flask is heated so that the heptane boils gently so that heptane vapor goes up the side tube of the extractor, condenses above the extractor and continuously adds clean distilled heptane to the extractor. The extraction is generally carried out for at least about 12 hours. Then the apparatus is allowed to cool. The sample tube is removed and placed in a vacuum oven at about 80° C. until dry, generally about 4 to 5 hours. The weight of polymer remaining in the tube is then determined. This weight subtracted from the original weight of the polymer equals the weight of soluble polymer, i.e. polymer extracted by the heptane. The Heptane solubles weight percent is equal to the weight of the dissolved, i.e. solubilized, polymer divided by the weight of the polymer subjected to the extraction times 100.

Example I

Preparation of FlSiMe$_2$Cl

Here 5 g (30 mmol) of fluorene was dissolved in 150 ml of diethyl ether and reacted with 18.8 ml of butyllithium (1.6M in hexane). After stirring for three hours, the solvent was evaporated to yield a yellow powder. Then 5 g of Me$_2$SiCl$_2$ (39 mmol) was dissolved in 200 ml of anhydrous pentane and then solid fluorenyl lithium salt was added. After stirring for one hour, the mixture was filtered to remove precipitated lithium chloride. Evaporation of the solvent yielded a yellow oil which was characterized by GC/MS as fluorenyldimethylchlorosilane.

Example II

Preparation of FlSiMe$_2$Cp

Here 4.7 g of crude FlME$_2$SiCl from Example I was dissolved in 200 ml of diethyl ether and 2.6 g (30 mmol) of CpNa, i.e. cyclopentadienyl sodium was added. After stirring for 12 hours, the mixture was washed with water to remove NaCl and the organic layer was dried over Na$_2$SO$_4$. Evaporation of the solvent yielded an orange oil, characterized by GC/MS as 9-(dimethyl cyclopentadienyl silyl)fluorene, i.e. FlSi(Me)$_2$, which could also be called 1-(9-fluorenyl)-1-cyclopentadienyl-1,1-dimethyl silane.

Example III

Preparation of FlSiPh$_2$Cl

Here 5 g (30 mmol) fluorene, dissolved in dimethyl ether, was reacted for three hours with 18.8 ml of butyllithium (1.6M in hexane). The solvent was evaporated to yield yellow fluorenyl lithium. Then 11.4 g (45 mmol) of Ph$_2$SiCl$_2$, i.e. diphenyl dichloro silane, was dissolved in 200 ml of pentane and the solid fluorenyl lithium was added in one portion to the pentane solution. After stirring for one hour, the mixture was filtered, the precipitated LiCl was eluated with 50 ml of ether, and the solvent evaporated from the combined organic layers to yield a yellow powder characterized by GC/MS as FlSiPh$_2$Cl, i.e. fluorenyl-diphenyl chlorosilane. Crystallization in pentane yields colorless crystals of the product, from which a H-NMR-spectra could be obtained.

Example IV

Preparation of FlSiPh$_2$Cp

To a solution of 2 g (5 mmol) of the FlSiPh$_2$Cl of Example III in 50 ml of diethyl ether and 10 ml of HMPT, 1.2 g (14 mmol) of CpNa was added. The mixture was stirred for 12 hours and then washed with 30 ml water, saturated with CuSO$_4$, and again washed with water. After drying the organic layer with Na$_2$SO$_4$, the solvent was evaporated to yield a white solid, which was characterized by GC/MS as FlCpSiPh$_2$ accompanied with 10% of bisfluorene.

Example V

Polymerizations were carried out to compare the effects of different metallocenes on the polymerization of propylene. The metallocenes evaluated were (fluorenyl)dimethylsilyl(cyclopentadienyl)zirconium dichloride, (fluorenyl)diphenylsilyl(cyclopentadienyl)zirconium dichloride, and (fluorenyl)dimethylmethylene(cyclopentadienyl)zirconium dichloride, which is often also referred to as (fluorenyl)isopropylidene(cyclopentadienyl)zirconium dichloride. The metallocenes were prepared by reacting a di-alkali metal salt of the respective fluorenyl cyclopentadienyl bridged compound with ZrCl$_4$ in a liquid diluent, such as diethyl ether. The polymerizations were conducted under particle form conditions using propylene as the diluent. The metallocene was used in conjunction with methylaluminoxane cocatalyst. The cocatalyst was employed as a 1.1 molar solution. In the polymerization using the dimethylsilyl bridged metallocene, 8 mL of the MAO was employed. The aluminum to zirconium ratio was 854. In the polymerization using the diphenylsilyl bridged metallocene, 1 mL of the MAO solution was employed and the aluminum to zirconium ratio was 1,119. In the polymerization using the dimethyl methylene bridged metallocene, 3 mL of the MAO solution were employed for an aluminum to zirconium ratio of 595. The silyl bridged polymerizations were carried out at a temperature of 70° C. and the dimethyl methylene bridged metallocene polymerization was carried out at 80° C. All three polymerizations were carried out for one hour. The polymerizations were conducted in the presence of hydrogen. The diluent was flashed off and the total polymer recovered was tested for various characteristics. The results obtained in the three polymerizations are summarized in Table I.

propylene produced using the dimethyl methylene bridged metallocene. It would also explain the signifi-

TABLE I

|  | Me2Si(fluor)CpZrCl2 | Ph2Si(fluor)CpZrCl2 | Me2C(fluor)CpZrCl2 |
| --- | --- | --- | --- |
| Activity (g PP/g Metallocene) | 39,283 | 229,130 | 108,125 |
| Melt Flow (ASTM D1238) | 77.54 | 412.89 | 77.5 |
| Mw from GPC | 65,740 | 46,490 | 63,200 |
| HI from GPC | 1.83 | 1.95 | 1.8 |
| Density | 0.8733 | 0.8724 | 0.8771 |
| Xylene Solubles (wt %) | 71.6 | 63.3 | 29.8 |
| Heptane Solubles (wt %) | 90.65 | 100 | 9.9 |
| Hardness Shore D | 43 | 43 | 62 |
| Flexural Modulus (MPa) | 158.6 | 151.7 | 445.9 |
| Tensile Yield Strength (MPa) | 7.52 | 8.21 | 15.13 |
| Tensile Break Strength (MPa) | 2.62 | 4.55 | 6.76 |
| Tensile Yield Elongation (in) | 0.193 | 0.2023 | 0.133 |
| Tensile Break Elongation (in) | 0.5402 | 0.4517 | 0.392 |

Figure 2:
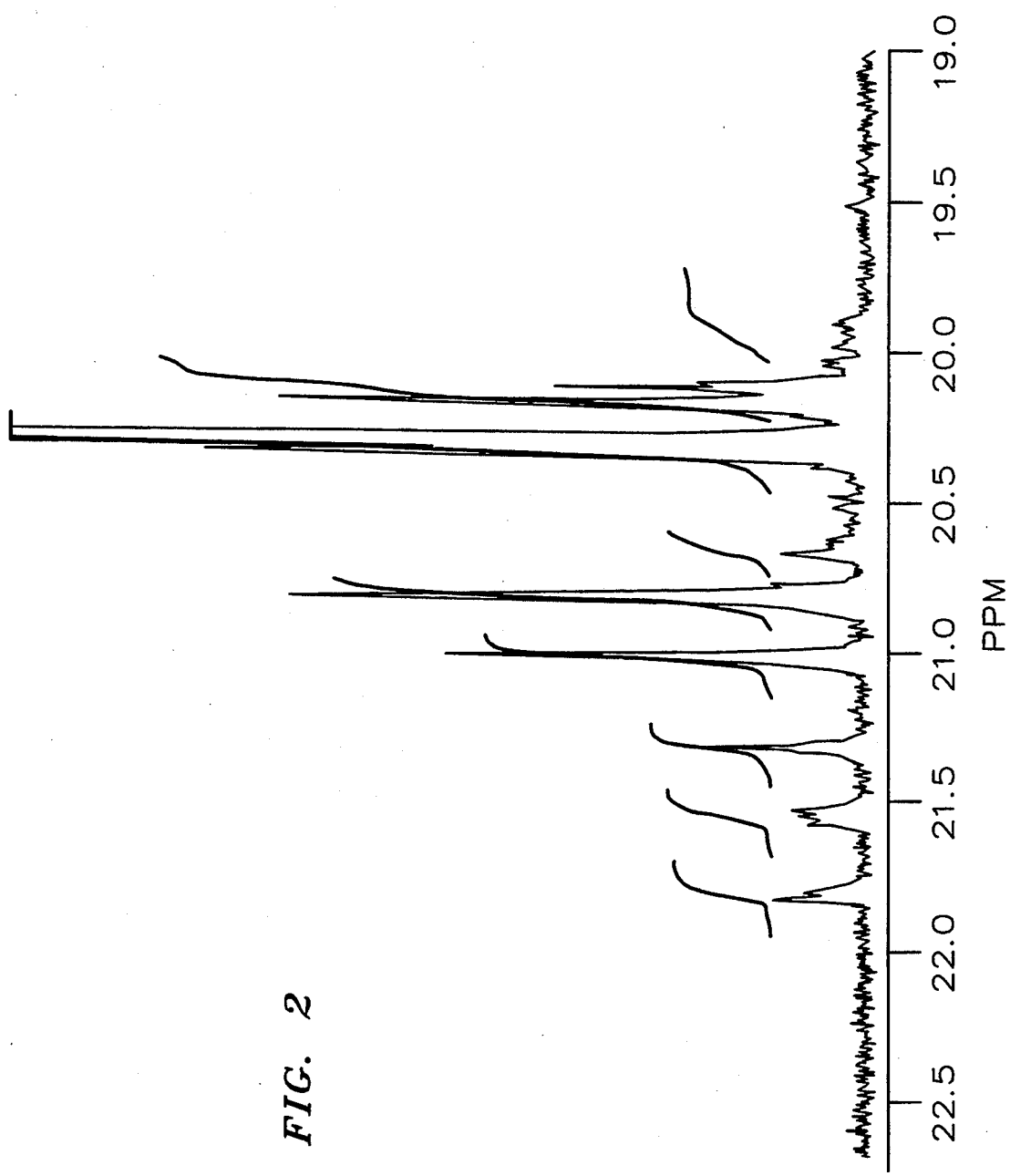
FIG. 2 is a $C_{13}$NMR spectra of a syndiotactic polyproylene produced using (fluorenyl)diphenylsilyl(cyclopentadienyl)zirconium dichloride.
Figure 3:
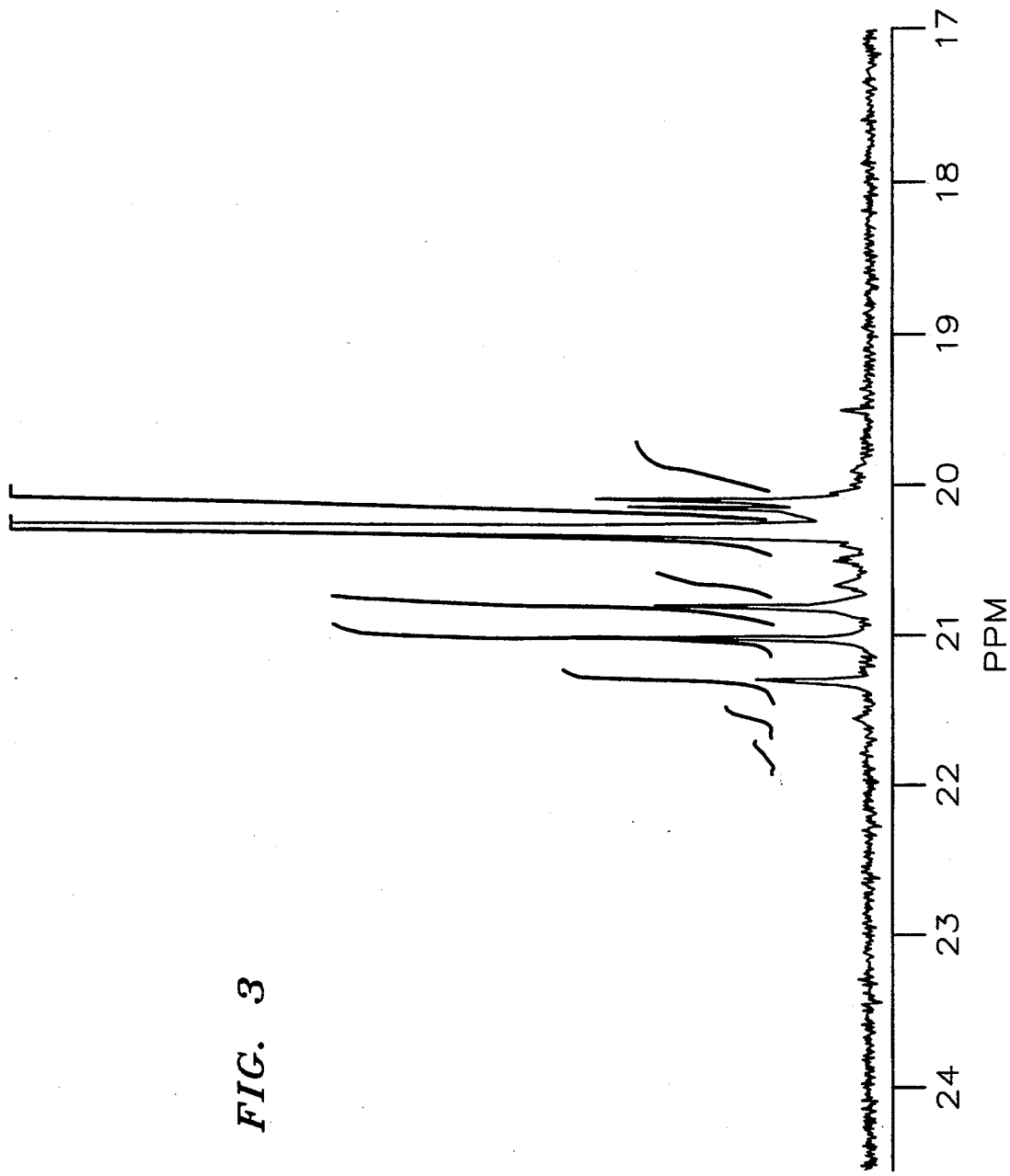
FIG. 3 is a $C_{13}$NMR spectra of a syndiotactic polypropylene produced using (fluorenyl)dimethylmethylene(cyclopentadienyl)zirconium dichloride.

The data reveals that the diphenylsilyl bridged metallocene produced a polymer having a lower weight average molecular weight than the dimethyl methylene bridged metallocene or the dimethylsilyl bridged metallocene. Surprisingly, even though all three make syndiotactic polypropylene, there is a vast difference between the xylene solubles of the polymers produced using the silyl bridged metallocenes and the polymer produced using the dimethyl methylene bridged metallocene. There is also a significant difference between the hardness and the flexural modulus of the polymers produced with the silyl bridged metallocenes and the dimethyl methylene bridged metallocene. The syndiotactic polypropylenes produced using the silyl bridged metallocenes thus have low stiffness even, though they are substantially syndiotactic. In order to obtain a further understanding of the reason for these differences, the polymers were subjected to $C_{13}$NMR analysis. The NMR spectra are shown in FIGS. 1-3. Table II reports some of the results obtained from that NMR analysis.

TABLE II

| Bridge | Me2Si | Ph2Si | Me2C |
| --- | --- | --- | --- |
| Isotacticity [% mm] | 5.11 | 6.74 | 2.40 |
| Heterotacticity [% mr] | 18.65 | 18.98 | 15.89 |
| Syndiotacticity [% rr] | 76.24 | 74.28 | 81.71 |
| Meso Content [% m] | 14.43 | 16.23 | 10.34 |
| Racemic Content [% r] | 85.57 | 83.77 | 89.66 |
| Randomness Index | 0.76 | 0.7 | — |
| Isotactic Block | 1.55 | 1.71 | 1.30 |
| Syndiotactic Block | 9.18 | 8.83 | 11.28 |
| Relative Syndiotactic Block Length | 0.81 | 0.78 | 1.0 |

It will be noted that while the % rr, shows all three polymers to be substantially syndiotactic, there was a significant difference between the average length of the syndiotactic blocks of the polymers obtained from the silyl bridged metallocenes and the polymer obtained using the dimethyl methylene bridged metallocene. The shorter syndiotactic blocks of the polymers produced with the silyl bridged metallocenes is theorized to be due to more frequent interruptions in the syndiotactic structure. It is theorized by the inventors that it is the shorter syndiotactic blocks that lead to the unusual physical properties of the polymers obtained with the silyl bridged metallocenes. It is theorized that because of the more frequent interruptions, the shorter the average syndiotactic lengths and the more the polymer properties deviate from normal crystalline polymer. Accordingly, this would explain the fact that the polypropylene produced from silyl bridged metallocenes have significantly higher xylene solubles than the polycant differences in the flexural modulus of the polymers produced using metallocenes having the two different types of bridges. The difference in the crystallinity of the polymers produced using the silyl bridged metallocenes and the dimethyl methylene bridged metallocene has also been demonstrated by the use of Differential Scanning Colorimetry (DSC). The DSC for the polymer produced using the methylene bridged metallocene has a noticeable peak at one location. The DSC for the polymer produced using the silyl bridged metallocenes had only minor hills rather than any one single peak. The polymers produced using the silyl bridged metallocenes are also unique in that although they have some properties which are analogous to those of atactic polypropylene, they are not sticky like the polymers generally referred to as atactic polypropylene.

Subsequent polymerizations using both the silyl bridged and the dimethyl methylene bridged metallocenes have revealed that for both catalysts the syndiotactic block length and the degree of crystallinity decreases as the polymerization temperature is increased; however, at a given polymerization temperature the block length of a polymer obtained using a silyl bridged metallocene was always shorter than that of the polymer obtained with the methylene bridged metallocene. Similarly, the randomness index of the syndiotactic blocks tends to increase with polymerization temperature for both types of bridged metallocenes; however, at a given temperature the randomness index of the polymer obtained with the silyl bridged metallocenes was greater than that of the polymer obtained with the dimethyl methylene bridged metallocene. Yet another difference was noted between the polymers produced with the methylene bridged metallocene and the silyl bridged metallocene. With the dimethyl methylene bridged metallocene there was little variation in the molecular weight distribution of the polymer produced over the temperature range of 30° C. to 80° C. In contrast, the polypropylene produced at 40° C. using the dimethyl silyl bridged metallocene had a much broader molecular weight distribution than polypropylene produced using that same silyl bridged metallocene at lower and higher temperatures. It was further observed that once the hydrogen level reached a certain point, the dimethyl silyl bridged metallocene produced a much broader molecular weight distribution polymer.

Example VI

Preparation of
9-(2,7-t-butylfluorenyl)dimethylchlorosilane and
diphenyl chlorosilane 5 g of 2,7-di-t-butylfluorene (18 mmol) was dissolved in 100 mL of ether and slowly mixed with 11.2 mL of butyllithium (1.6M in hexane). After a period of reaction of 4 hours, the solvent was removed and the solid lithium compound was added to a solution of 2.8 g of dimethyldichlorosilane in 200 mL of ether. After a reaction time of 1 hour, the reaction mixture was filtered over sodium sulfate and the precipitate was washed twice, in each case, with 100 mL of ether. Colorless crystals were obtained after concentration of the solution by evaporation followed by crystallization at $-30°$ C. (yield: 85–90%). The structure was confirmed by GC/MS and $H^1$ NMR and $C^{13}$ NMR.

Preparation of the 2,7-di-t-butylfluorenyldiphenylchlorosilane was carried by an analogous method using diphenyldichlorosilane instead of dimethyldichlorosilane. The product was formed as an orange oil (yield: 85%). The structure was confirmed by GC/MS and $H^1$NMR and $C^{13}$NMR.

Example VII

The chlorosilanes of Example VI were each reacted with cyclopentadienyl sodium to produce the corresponding silyl bridged (2,7-di-t-butylfluorenyl) (cyclopentadienyl) compounds. The reactions were carried out by dissolving the chlorosilane in ether and then mixing with the cyclopentadienyl sodium and stirring for about 4 hours. The reaction mixture was then hydrolyzed with saturated ammonium chloride solution. The organic phase was washed with water and then dried over sodium sulfate. The compounds were both obtained as white solids. They were characterized using GC/MS, $H^1$NMR and $C^{13}$NMR.

Figure 4:
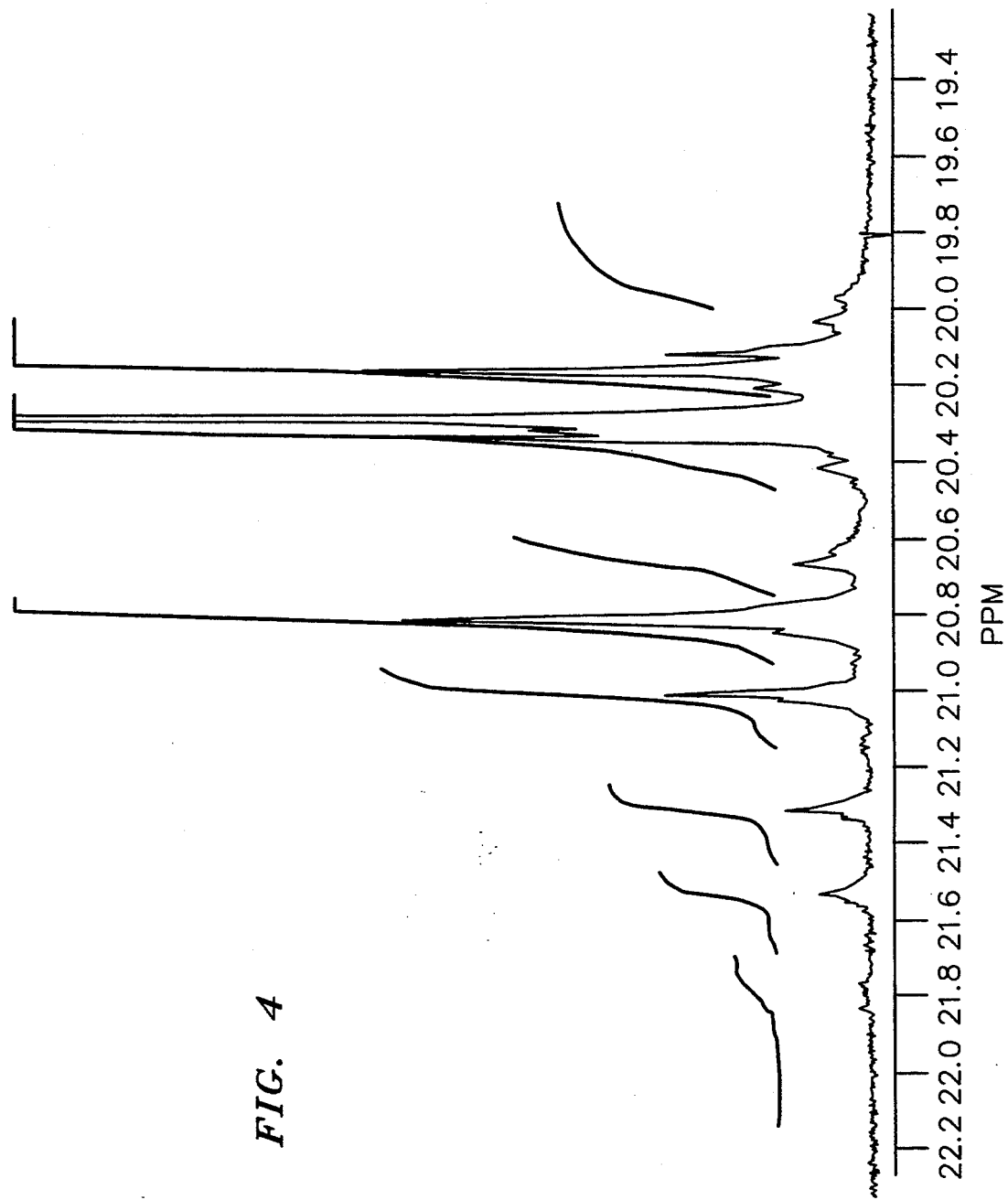
FIG. 4 is a $C_{13}$NMR spectra of a syndiotactic polypropylene produced using (2,7-di-t-butylfluorenyl)-dimethyl silyl(cyclopentadienyl)zirconium dichloride.
Figure 5:
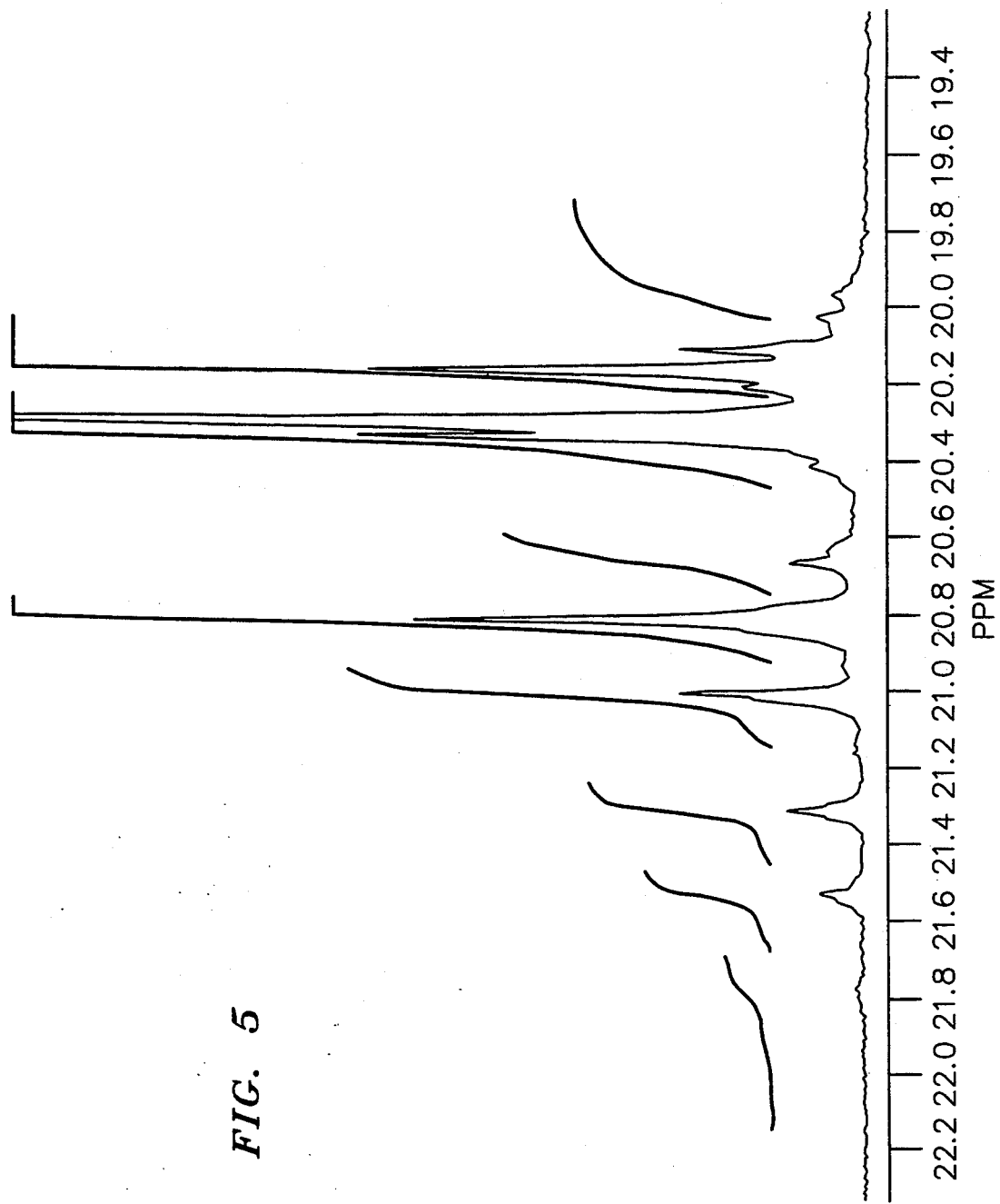
FIG. 5 is a $C_{13}$NMR spectra of a syndiotactic polypropylene produced using (2,7-di-t-butylfluorenyl)diphenylsilyl(cyclopentadienyl)zirconium dichloride.

The silyl bridged (2,7-di-t-butylfluorenyl) (cyclopentadienyl) compounds were each individually used to prepare metallocenes using techniques analogous to that described in Example V. Then polymerizations of propylene were conducted to determine the effectiveness of the metallocenes. The polymerization conditions were analogous to those used in Example V. The liquid diluent was flashed and the total recovered polymer was subjected to $C^{13}$NMR analysis. FIG. 4 is a copy of the NMR spectra for the dimethyl silyl bridged metallocene and FIG. 5 is a copy of the NMR for the diphenyl silyl bridged metallocene. Some of the data obtained from the NMR spectra are summarized in Table III.

TABLE III

| Silyl Bridged (2,7-di-t-butylfluorenyl) (cyclopentadieneyl) zirconium dichloride | | |
|---|---|---|
| Bridge | Ph$_2$Si | Me$_2$Si |
| Isotacticity [% mm] | 5.12 | 4.96 |
| Heterotacticity [% mr] | 25.28 | 25.41 |
| Syndiotacticity [% rr] | 69.60 | 69.63 |
| Meso Content [% m] | 17.76 | 17.69 |
| Racemic Content [% r] | 82.24 | 82.33 |
| Randomness Index | 0.866 | 0.873 |
| Isotactic Block | 1.41 | 1.39 |
| Syndiotactic Block | 6.51 | 6.48 |

These results indicate that the presence of the alkyl substituents on the fluorenyl reduces the selectivity to syndiotactic microstructure somewhat; however, the polymers are still substantially syndiotactic. The average syndiotactic block length was again very low which indicates that the polymers are more analogous to those made with the silyl bridged metallocene of Example V than to the polymer made with the control metallocenes of Example VI.

Example VIII

Preparation of
9-(2,7-di-t-butylfluorenyl)-9'-fluorenyldimethylsilane 3.4 g (20 mmol) of fluorene was dissolved in 100 mL of ether and mixed with 13 mL of butyllithium (1.6 M in hexane). After stirring for 4 hours, the solvent was removed and the yellow fluorenyllithium was dried in a high vacuum.

5 g (13.5 mmol) of 9-(2,7-di-t-butylfluorenyl)dimethylchlorosilane was dissolved in 100 mL of ether and mixed with 10 mL of TMEDA. The solid fluorenyllithium was added to this in portions and the reaction mixture was allowed to stir for 4 hours at room temperature. Then the mixture was hydrolyzed with 100 mL of saturated ammonium chloride solution; the organic phase was washed several times with water and then dried over sodium sulfate. The bright yellow solution obtained was concentrated by evaporation to about one-half of its volume and then crystallized at $-30°$ C. The product was recovered in the form of a white powder (yield: 85%).

The silyl bridged fluorenyl compound was used to prepare a zirconium metallocene using a technique analogous to that used in Example V and the metallocene was used to polymerize propylene under conditions analogous to those used in Example V. After the polymerization, the liquid diluent was flushed and the total recovered polymer was subjected to analysis.

Figure 6:
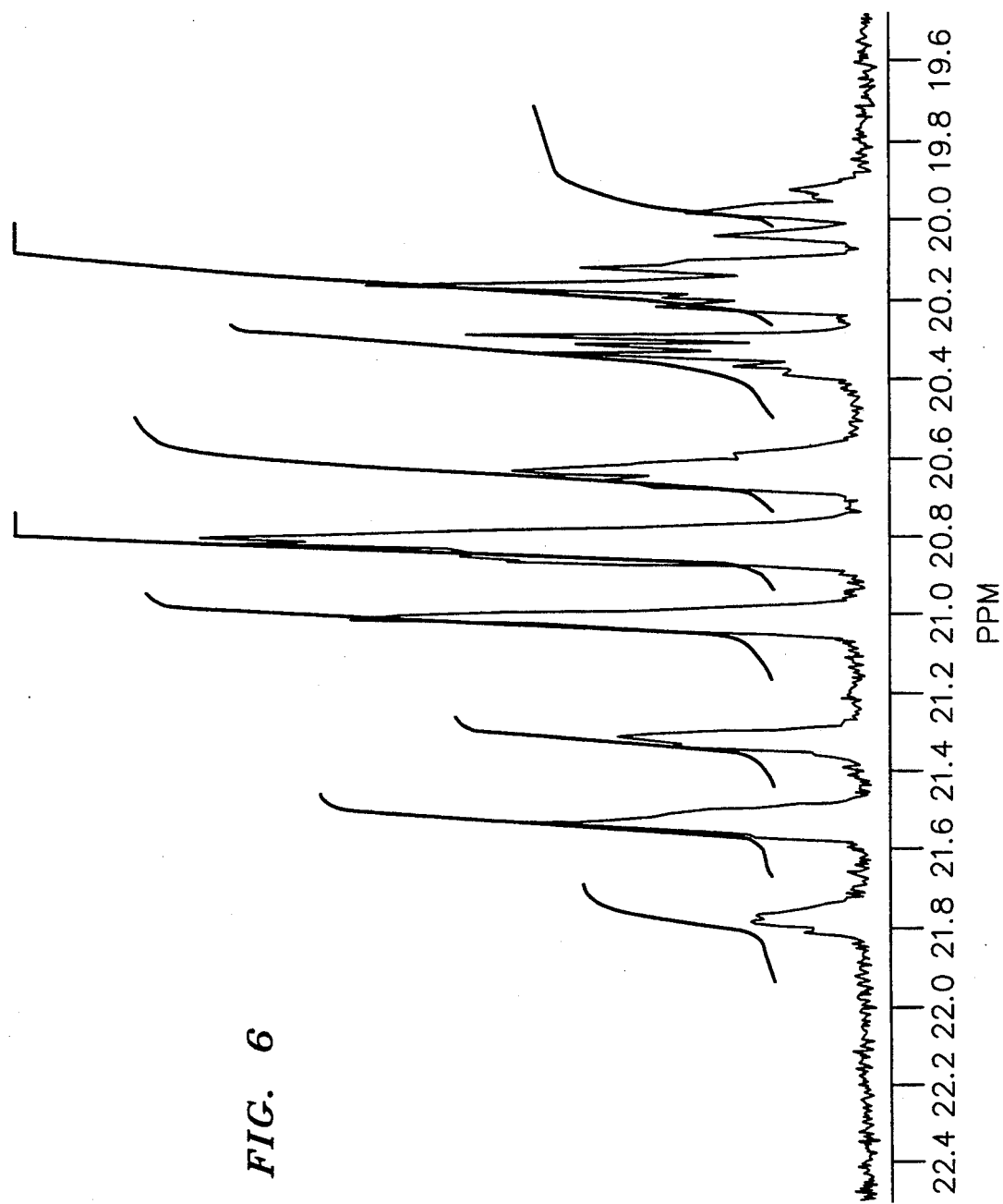
FIG. 6 is a $C_{13}$NMR spectra of a syndiotactic polypropylene produced using (2,7-di-t-butylfluorenyl)-dimethylsilyl(fluorenyl)zirconium dichloride.

The $C_{13}$NMR spectra of the polymer is shown in FIG. 6. The NMR spectra reveals isotacticity of 18.87%, heterotacticity of 48.67% and syndiotactivity of 32.46%. The meso (m) content was 43.21% and the recemic (r) content was 56.79%. The randomness compared to a Bernoullian index of 1 was 0.992. The average syndiotactic block length was 2.33.

Example IX

Using a method analogous to that of Example VIII, 9-(2,7-di-t-butylfluorenyl)-9'-fluorenyldiphenylsilane was prepared. (Yield: 81%).

That which is claimed is:

1. A process for polymerizing an olefin having at least 3 carbon atoms comprising contacting said olefin under suitable polymerization conditions with a catalyst system comprising a bridged sandwich-bonded metallocene of a metal selected from Group IV of the Periodic Table, said metallocene being selected from bridged sandwich-bonded metallocenes of a metal selected from Group IV of the Periodic Table in which the organic ligand is selected from compounds of the formula

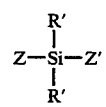

wherein Z and Z' are different, Z is an unsubstituted fluorenyl radical or a symmetrically substituted fluorenyl radical and Z' is an unsubstituted cyclopentadienyl radical, a symmetrically substituted cyclopentadienyl radical, an unsubstituted fluorenyl radical, or a symmetrically substituted fluorenyl radical; each R' is the same or different organo radical having 1 to 20 carbon atoms.

2. A process according to claim 1 wherein propylene is polymerized.

3. A process according to claim 2 wherein a propylene homopolymer is produced.

4. A process according to claim 3 wherein Z is unsubstituted fluoreneyl, Z' is unsubstituted cyclopentadienyl and each R' is a methyl radical.

5. A process according to claim 4 wherein said catalyst system comprises a cocatalyst comprising an alkylaluminoxane.

6. A process according to claim 5 wherein said metallocene is dimethyl silyl (fluorenyl) (cyclopentadienyl) zirconium dichloride.

7. A process according to claim 3 wherein Z is unsubstituted fluorenyl, Z' is unsubstituted cyclopentadienyl, and each R' is a phenyl radical.

8. A process according to claim 7 wherein said catatlyst system comprises a cocatalyst comprising an alkyl aluminoxane.

9. A process according to claim 8 wherein said metallocene is diphenyl silyl (fluorenyl) (cyclopentadienyl) zirconium dichloride.

10. A process according to claim 3 wherein Z is a 2,7-dialkyl substituted fluorenyl radical.

11. A process according to claim 10 wherein Z' is an unsubstituted fluorenyl radical.

12. A process according to claim 10 wherein Z' is an unsubstituted cyclopentadienyl radical.

13. A process according to claim 12 wherein each R' is a phenyl radical and the metal of the metallocene is zirconium.

14. A process according to claim 13 wherein said metallocene is (2,7, di-tert-butyl fluorenyl) diphenyl silyl (cyclopentadienyl) zirconium dichloride and said catalyst system comprises a cocatalyst comprising an alkylaluminoxane.

* * * * *